United States Patent [19]

Nettekoven

[11] Patent Number: 5,591,141
[45] Date of Patent: Jan. 7, 1997

[54] SUCTION COAGULATOR BENDING TOOL

[75] Inventor: William S. Nettekoven, Sandy, Utah

[73] Assignee: MegaDyne Medical Products, Inc., Draper, Utah

[21] Appl. No.: 529,227

[22] Filed: Sep. 15, 1995

[51] Int. Cl.$^6$ .................................................. A61M 25/00
[52] U.S. Cl. .......................... 604/280; 604/264; 604/95; 72/369
[58] Field of Search ................................... 604/280, 281, 604/264, 95, 35, 52, 53, 272; 72/369

[56] References Cited

U.S. PATENT DOCUMENTS

| 1,903,436 | 4/1933 | Brown . | |
|---|---|---|---|
| 2,824,475 | 2/1958 | Rolando . | |
| 3,470,876 | 10/1969 | Barchilon | 604/95 |
| 3,521,620 | 7/1970 | Cook | 604/280 X |
| 4,898,577 | 2/1990 | Badger et al. | 604/282 X |
| 5,201,210 | 4/1993 | Stein, III . | |

FOREIGN PATENT DOCUMENTS

| 876800 | 7/1949 | Germany . |
|---|---|---|
| 63-192519 | 8/1988 | Japan . |
| 1-186221 | 7/1989 | Japan . |

OTHER PUBLICATIONS

Publication "What do you Bend on a Bender?" Pines Engineering Co., Inc., Aurora, Illinois May 11, 1962.

*Primary Examiner*—John D. Yasko
*Attorney, Agent, or Firm*—John L. Sigalos

[57] ABSTRACT

A combination suction coagulator and dedicated bending tool for customizing working surfaces of suction coagulator instruments. A working extension of the coagulator is provided with an improved insulating coating and is adapted for customized bending with a dedicated tool that has at one end a recess with a centrally located mandrel pin for insertion into the hollow interior of the coagulator extension. A curved channel is provided in cooperative association with the recess and mandrel pin so as to limit the radius of any bend that may be made by the user. That, in combination with the form-fitting mandrel pin provide a ready way of bending the distal extremity of the coagulator extension while maintaining its internal geometrical integrity. The tool also includes a custom stylet for use in cleaning accumulated debris from the interior of the working extension.

12 Claims, 2 Drawing Sheets

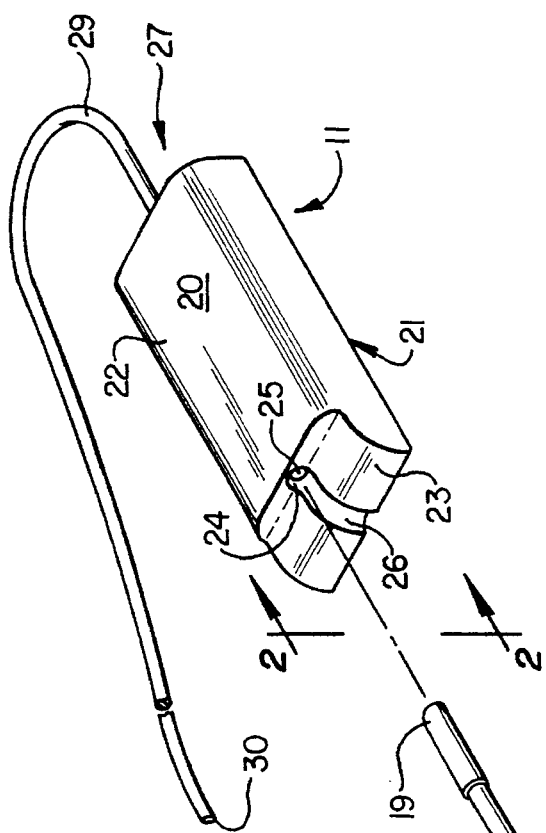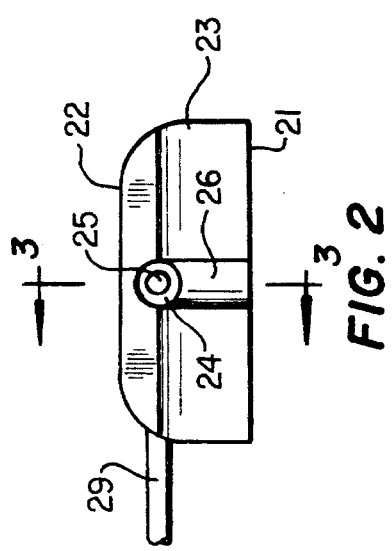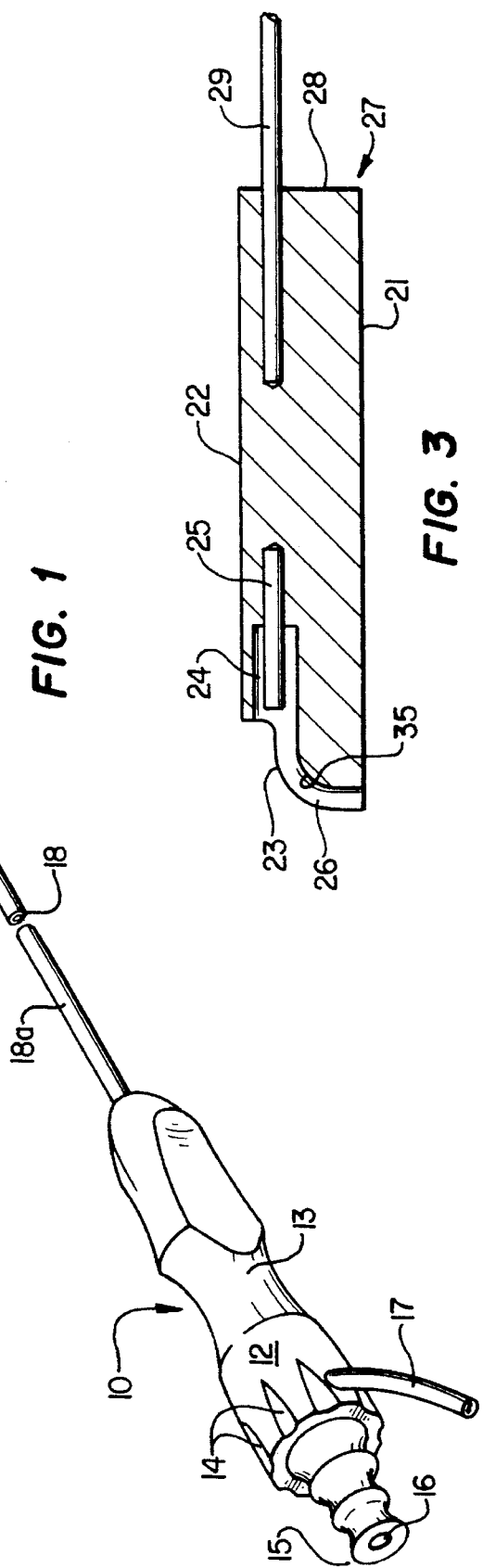

SUCTION COAGULATOR BENDING TOOL

This invention relates to a combination suction coagulator associated custom bending tool; and it more particularly relates to such a suction coagulator that includes a PTFE (poly tetrafluorethylene) insulated extremity that is custom bendable with a dedicated bending tool, the combined coagulator and tool being disposable after each use.

BACKGROUND OF THE INVENTION

As is known to those skilled in the art, there is a high level of concern in medical circles for achieving high levels of cleanliness and sterilization. Thus, subject to considerations of cost and availability, there has been a continuing trend toward making surgical implements disposable.

A variety of proposals have heretofore been made for providing suction coagulating instruments for use in sinus and other nasal related procedures. Such instruments have employed a gripping member, or handle, for use by a surgeon in manipulating the instrument. Extending forward from such member is a hollow tubular member having a distal extremity for contacting patient tissue, while at the proximal end there has been provision for connection of a repository for received fluids interposed between the instrument and a suction source such as a vacuum pump. Provision has also been made for controllably applying electrical current to the distal end of the tubular member so that the surgeon can optionally remove unwanted fluids such as blood and coagulate exposed surfaces/fluids to control bleeding.

As is known to those skilled in the art, suction/coagulation instruments are more effective when their extending extremities are positioned essentially normally (i.e., at right angles) to the patient's work surface. Accordingly, there has been a need to include a provision of bendability to the distal extremities of the extending tubular members so as to accommodate differences in patient physiologies.

BRIEF SUMMARY OF THE INVENTION

The improved suction coagulator according to the invention hereof includes a handle portion for gripping and manipulation, a hollow tubular extension having a proximal end mounted within the handle and a distal portion extending outwardly from the handle. Included within the handle is an aperture in communication with the interior of the tubular extension for controlling suction therein imparted by a separate source of vacuum such as a conventional vacuum pump.

A dedicated bending tool is provided for manipulation in cooperative combination with the distal portion of the tubular extension so as to provide a facilitated way of custom bending the distal portion according to the particular physiology of a patient on whom a surgical procedure is to be employed. The bending tool is generally elongated and includes at one end a recess that is slightly larger in diameter than the outer diameter of the distal end of the tubular extension. Centrally located within the recess is a mandrel pin that is configured to conform to the interior cross sectional geometry of the tubular extension while being only slightly lesser in cross section so as to permit the end of the tubular extension to be slid thereover while retaining engagement therewith. Extending in axial alignment with the mandrel pin is a channel that essentially conforms to the exterior surface shape of the tubular extension so as to receive the same in mating and engaging relationship as the distal end of the tubular extension is mounted on the mandrel pin and the tool is manipulated to bend the distal end. Thus, the tubular extension is trapped by the combination of mandrel pin and channel so that it can be bent without collapsing or significantly changing the interior cross section of the tubular extension. In addition, the geometry of the channel and mandrel pin are such that a curved radius of the channel controls the maximum amount of bend allowed so the tubing does not break or collapse. By inserting the tubular extension up to its maximum depth, bending slightly, pulling the tubular extension out a small distance, bending again and then repeating this process, the precise angle and bend required by a physician can be achieved. Thus, a custom bend according to the physiology of each patient may be provided, the combination tool and instrument being discarded after use and a new combination being provided for the next patient.

OBJECTS AND FEATURES OF THE INVENTION

It is one general object of the invention to improve medical suction coagulators.

It is yet another object of the invention to facilitate customization of suction coagulators to fit the physiology of each individual patient.

It is another object of the invention to reduce danger of disease transmission by making suction coagulators and their attendant tools disposable.

Accordingly, in accordance with one feature of the invention, a suction coagulator and its customizing tool are combined, thereby facilitating availability and use.

In accordance with another feature of the invention, the customizing tool is dedicated to the geometrical configuration of the suction coagulator, thereby facilitating its use.

In accordance with another feature of the invention, the customizing tool is generally elongated and is fitted at one end with a mandrel pin and associated bending channel thereby to provide for controlled incremental bending while maintaining the internal cross section of an engaging tubular extension essentially unchanged.

In accordance with still another feature of the invention, the customizing tool includes a cooperative flexible stylet at the opposite end of the tool from that of the mandrel pin so as to provide for ready removal of unwanted material that may otherwise accumulate within the tubular extension during an operative procedure.

These and other objects and features of the invention will be apparent from the following description, by way of example of a preferred embodiment, with reference to the drawing.

BRIEF DESCRIPTION OF THE DRAWING

FIG. 1 is a perspective view depicting the suction coagulator instrument and bending tool according to the invention;

FIG. 2 is a section taken along section lines 2—2 of FIG. 1;

FIG. 3 is a side sectional view taken along section lines 3—3 of FIG. 2;

DESCRIPTION OF A PREFERRED EMBODIMENT

Figure 4:
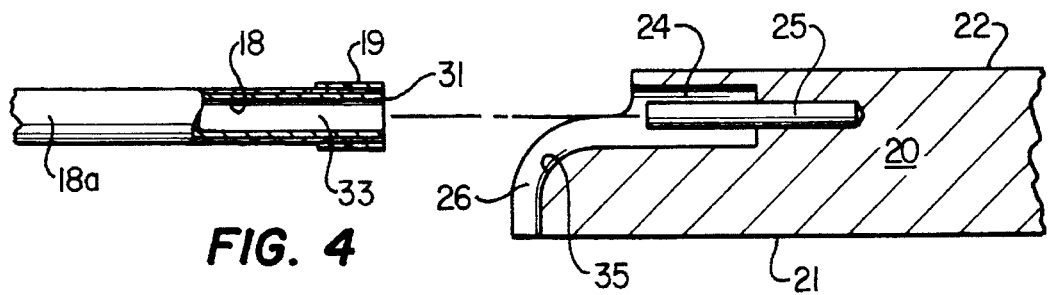
FIG. 4 is a view illustrating the forward part of the section of FIG. 3 together with the forward end of the suction coagulator tubing prior to engagement therebetween.

Now turning to the drawing, and more particularly FIG. 1 thereof, it will seen to illustrate a combined suction coagulator instrument 10 and custom bending tool 11. Suction coagulator 10 is seen to include a handle portion 12 that may be made of any of a variety of well known plastic or similar materials such as polystyrenes, polycarbonates, and polyamides, but ABS lacrylonitrile-butadiene-styrened polymers are preferred. Its exterior geometrical configuration includes generally concave surface 13 and concave flutes 14 which are provided to facilitate holding and manipulation. At proximal end 15 there is provided for connection to a source of suction, an aperture 16 that is in internal communication with the interior of hollow tubular extension 18; and a conventional thumb hole (not shown) is included to provide the user with a ready way of controlling suction during use. Extension 18 is preferably circular in cross-section, although non-circular geometries can also be utilized. Included on the exterior surface of extension 18 is a thin insulating coating 18a, which is preferably a thin polyolefin shrink polymer such as polyethylene or polypropylene. Also shown at the extreme distal end of extension 18 is a further coating 19 over coating 18a. Such coating 19 extends for only 1 or 2 centimeters and is a polytetrafluoroethylene (PTFE) to help minimize eschar buildup and adherence. Coating 19 is optional. Power cable 17 is provided for connection to a conventional source of coagulating power.

Cooperative custom bending tool 11 is seen to include a main body 20 that is generally rectangular in shape with an essentially rectangular bottom 21 and a modified and partially curved top 22. Thus, as shown, its length is greater than its width which, in turn is greater than its thickness. At one end there is a first surface 23 in which there is formed a preferably cylindrical recess 24 within which there is axially disposed a mandrel pin 25; and extending outwardly and radially from recess 24 is curved channel 26. At the opposite end 27 there is a surface 28 (FIG. 3) through which there extends outwardly a flexible stylet 29 having a solid end 30 of diameter essentially equal to but minutely smaller than the internal diameter of hollow tubular extension 18 thus providing for convenient removal from the interior of extension 18 of any coagulated blood or tissue that may accumulate there during use. End 30 may be inserted into extension 18 and pushed therethrough to move undesired accumulations to the rear where they are sucked out by the aforementioned suction.

Now turning to FIG. 3, it will be seen to be a section taken along section lines 3—3 of FIG. 2. There, it will be seen are the aforementioned partially curved top 22, first surface 23, cylindrical recess 24, mandrel pin 25, curved channel 26, opposite end 27, surface 28 and flexible stylet 29.

Figure 5:
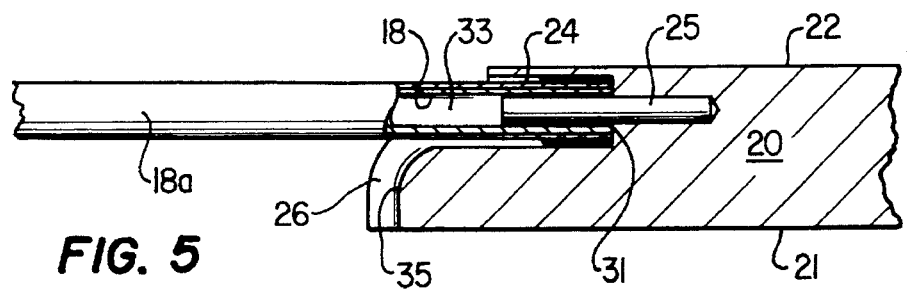
FIG. 5 is a view similar to that of FIG. 4 but with the forward end of the suction tubing in engagement with the bending tool and ready for bending.

FIG. 4 illustrates the combination of the instrument and tool with the distal end 31 of hollow tubular extension 18 in axial alignment with cylindrical recess 24 and mandrel pin 25 so as to be ready for the engagement as depicted in FIG. 5. There, in FIG. 5, the combination is shown with distal end in place within recess 24 so that the mandrel pin 25 slidably projects into the hollow interior 33. In this position, the combination is ready for bending force to be applied to tool main body 20 or to tubular extension 18.

Figure 6:
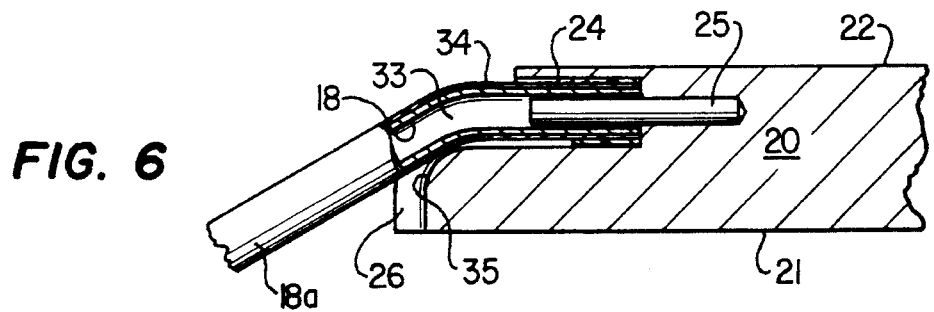
FIG. 6 is a view similar to that of FIG. 5 and illustrating partial bending of the suction tubing tip.

Bending of the distal portion 34 of tubular extension 18 is illustrated in FIG. 6 which shows the radius of the bend following the curvature 35 of curved channel 26. There, are seen the recess 24 within which is the axially positioned mandrel pin 25 that is configured to conform to the interior cross sectional geometry of the hollow interior 33 of the tubular extension 18 while being only slightly lesser in cross section so as to permit the end 34 of the tubular extension to be slid thereover while retaining engagement therewith. Also seen are the channel 26 that essentially conforms to the exterior surface shape of the tubular extension so as to receive the same in mating and engaging relationship as the distal end of the tubular extension is mounted on the mandrel pin and the tool is manipulated to bend the distal end. Thus, as shown in FIG. 6, the distal portion 34 of the tubular extension 18 is trapped by the combination of mandrel pin 25 and channel 26 so that portion 34 can be bent without collapsing or significantly changing the interior cross section of the tubular extension. In addition, the geometry of the channel 26 and mandrel pin 25 are such that the radius of curvature 35 controls the maximum amount of bend allowed so the tubing does not break or collapse. By inserting the distal portion 34 up to its maximum depth, bending slightly, pulling the tubular extension out a small distance, bending again and then repeating this process, the precise angle and bend required by a physician can be achieved. Thus, a custom bend according to the physiology of each patient may be provided, the combination tool and instrument being discarded after use and a new combination being provided for the next patient.

Figure 7:
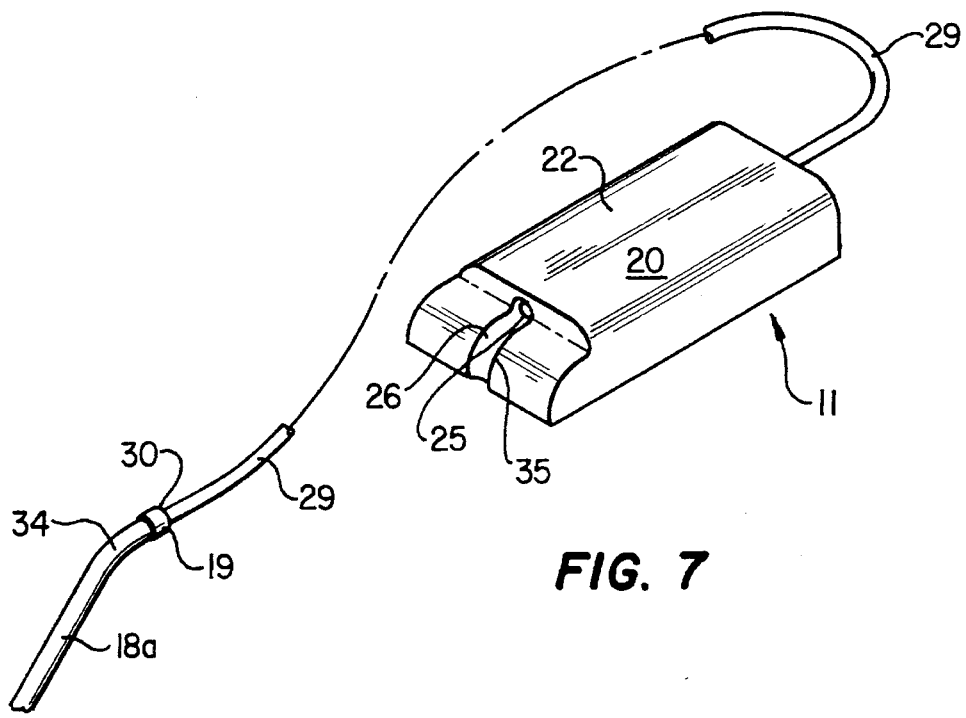
FIG. 7 is a perspective view of the preferred form of bending tool illustrating use of its flexible stylet in cleaning debris from the coagulator.

Now turning to FIG. 7, there is shown the use of the flexible stylet 29 in cleaning accumulated debris from the interior of the distal portion of tubular extension 18. As mentioned above, the customizing tool 11 includes a cooperative flexible stylet 29 at the opposite end of the tool from that of the mandrel pin 25 so as to provide for ready removal of unwanted material that may otherwise accumulate within the tubular extension 18 during an operative procedure. Also as mentioned above, flexible stylet 29 has a solid end 30 (FIG. 1) of diameter essentially equal to but minutely smaller than the internal diameter of hollow tubular extension 18 thus providing for convenient removal from the interior of extension 18 of coagulated blood or tissue that may accumulate there during use. End 30 may be inserted into extension 18 (as shown in FIG. 7) and pushed therein sufficiently to move any undesired accumulation to the rear of tube 18 where it is sucked out by the aforementioned suction accessory.

Although the invention hereof has been described by way of a preferred embodiment, it will be evident that other adaptations and modifications may be employed without departing from the spirit and scope thereof.

The terms and expressions employed herein have been used as terms of description and not of limitation; and thus, there is no intent of excluding equivalents, but on the contrary it is intended to cover any and all equivalents that may be employed without departing from the spirit and scope of the invention.

What is claimed is:

1. A suction coagulator comprising in combination:

(a) a suction instrument having a handle for manipulating said instrument, said instrument including a tubular extension having a proximal end mounted within said handle and a distal end extending away from said handle, said instrument including suction means communicating with said tubular extension for imparting suction thereto; and (b) bending tool means cooperatively associated with said tubular extension for engaging and bending said distal end of said tubular extension, said bending tool means having a recess therein dimensioned for slidable engagement with exterior surface of said tubular extension, said bending tool means having mandrel means axially mounted within said recess for extending into the interior of said tubular extension when said tubular extension is inserted within said recess, said bending tool means additionally having a radially curved channel extending away from said recess for receiving a part of said exterior surface of said tubular extension and for imparting a radial curvature to said part of said exterior surface of said tubular extension when said tubular extension is fitted to said tool and bending force applied thereto.

2. A suction coagulator combination according to claim 1 wherein said slideable engagement is contacting engagement.

3. A suction coagulator combination according to claim 1 wherein a surface area of said tubular extension adjacent said distal end of said tubular extension is coated with polytetrafluoroethylene.

4. A suction coagulator combination according to claim 1 wherein said tubular extension is of malleable metal.

5. A suction coagulator combination according to claim 4 wherein a surface area of said tubular extension adjacent said distal end of said tubular extension is coated with polytetrafluoroethylene.

6. A suction coagulator combination according to claim 1 wherein said mandrel means has an exterior surface geometry matching inside surface geometry of said distal end of said tubular extension for facilitating sliding of said distal end over said mandrel means.

7. A suction coagulator combination according to claim 1 wherein said bending tool means is substantially rectangular in geometry.

8. A suction coagulator combination according to claim 7 wherein said bending tool has a length dimension defined by a first surface at one end and a second surface at the opposite end.

9. A suction coagulator combination according to claim 8 wherein said bending tool has a width dimension defined by a first side and a second side opposite said first side.

10. A suction coagulator combination according to claim 8 wherein said mandrel is positioned at said first surface.

11. A suction coagulator combination according to claim 8 further including a flexible stylet attached to said bending tool at said second surface.

12. A suction coagulator combination according to claim 11 wherein said stylet has an exterior surface geometry substantially equal to the inside surface geometry of said distal end of said tubular extension.

* * * * *